Figure 1:
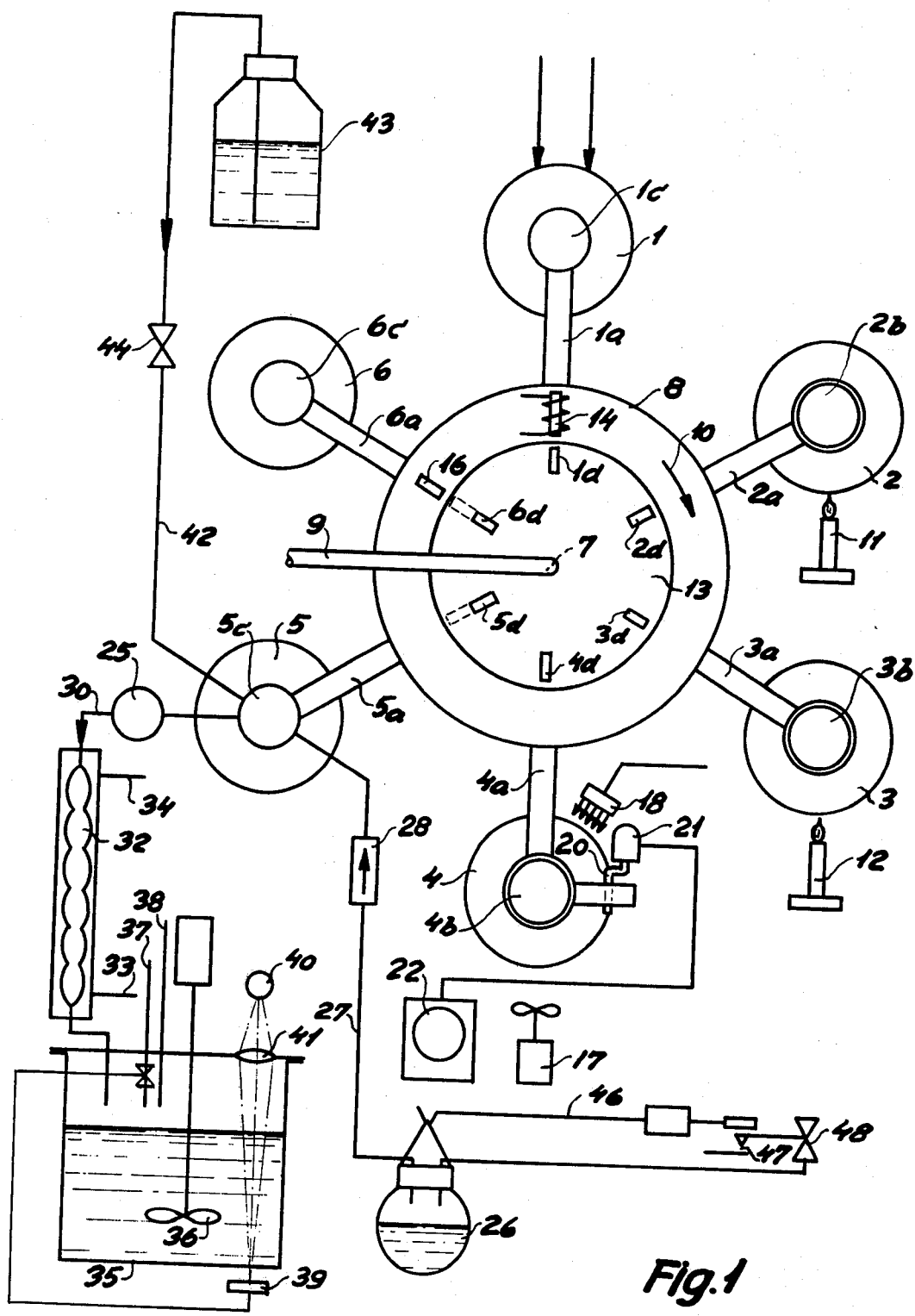

United States Patent [19]
Aegidius

[11] 3,964,869
[45] June 22, 1976

[54] ANALYTICAL APPARATUS FOR SERIAL DETERMINATION OF NITROGEN IN SAMPLES BY THE KJELDAHL METHOD

[75] Inventor: Poul Erik Aegidius, Helsinge, Denmark

[73] Assignee: N.K. Verwaltungs AG, Zug, Switzerland

[22] Filed: July 11, 1975

[21] Appl. No.: 594,937

Related U.S. Application Data

[63] Continuation of Ser. No. 447,179, Feb. 28, 1974, abandoned.

[30] Foreign Application Priority Data

Mar. 1, 1973  Denmark............................ 1119/73

[52] U.S. Cl................................. 23/253 R; 23/259
[51] Int. Cl.² ................. G01N 31/16; G01N 33/00
[58] Field of Search............ 23/253 R, 253 PC, 259, 23/230 R

[56] References Cited
UNITED STATES PATENTS

| | | | |
|---|---|---|---|
| 2,726,936 | 12/1955 | Bernheim.......................... | 23/253 R |
| 3,103,471 | 9/1963 | Asami............................ | 23/253 R X |
| 3,174,829 | 3/1965 | Stokstad........................... | 23/253 R |
| 3,335,097 | 8/1967 | Gillis............................ | 23/230 R X |
| 3,461,042 | 8/1969 | Martin et al. .................. | 23/253 R X |
| 3,616,273 | 10/1971 | Oita.............................. | 23/253 R X |
| 3,790,346 | 2/1974 | Ritchie........................... | 23/253 R |

Primary Examiner—Joseph Scovronek
Attorney, Agent, or Firm—Ladas, Parry, Von Gehr, Goldsmith & Deschamps

[57] ABSTRACT

This invention provides for an analytical apparatus for serial determination of nitrogen in samples by the Kjeldahl method, characterized in that it comprises from 4 to 7 flasks suspended vertically in a rotatable roundabout, each provided with a cover and a side tube extending into a common central container for the collection of combustion products, the roundabout being connected to a device which at regular intervals turns the roundabout one step forward to the next position, means for heating the flasks in one or two of the positions, means for blowing cooling air against the flasks, means for feeding diluent water to the flasks in a following position, means for introducing neutralising chemicals, means for generating and feeding steam to the flasks in the next following position, means for collecting and titrating the distillate, blowing means for emptying the flasks in the last position, and means for opening the covers on completion of the decomposition and for introducing diluent water into the flasks.

7 Claims, 2 Drawing Figures

ANALYTICAL APPARATUS FOR SERIAL DETERMINATION OF NITROGEN IN SAMPLES BY THE KJELDAHL METHOD

This is a continuation of application Ser. No. 447,179, filed Feb. 28,1974, now abandoned.

This invention relates to an analytical apparatus for serial determination of nitrogen in samples by the Kjeldahl method.

In the classical Kjeldahl method a sample of the compound, for instance 1 gram, is decomposed by heating in an inclined decomposition flask with a mixture of sulphuric acid, potassium sulphate and a decomposition catalyst. The flask is usually provided with a long neck in which the vapours from the boiling sulphuric acid mixture is condensed and refluxed to the decomposition mixture so that the loss of sulphuric acid is negligible. The flask is inclined to prevent that drops or splashes which may result from bumping are thrown out through the neck and cause loss of analytic liquid. It has been tried to prevent such splashing by providing a ball in the opening of the neck to seal the flask. But such a seal cannot be applied in the first stage of the decomposition on account of the strong frothing, and also during the subsequent stages of the decomposition the ball will rise now and then to allow formed gasses to escape, and then also splashed drops may be carried away. After completion of the decomposition the decomposition product is cooled down and diluted with water. The mixture is poured into a distilling flask and the remaining amount of sulphuric acid is neutralised with a base, for instance sodium hydroxide, which is added in excess to release ammonia. The released ammonia is stripped, for instance by steam distillation, and the accumulated distillate is titrated, the determined amount of ammonia being a measure of the nitrogen content in the sample.

The method is based on the fact that practically all organic nitrogen compounds break down pyrolytically in boiling sulphuric acid and form ammonium sulphate. Some nitrogen compounds are quite resistant to decomposition and in that case the break down may be accelerated by raising the boiling point of the sulphuric acid by addition of a salt, usually potassium sulphate. The decomposition rate may also be accelerated by adding a catalyst, and here mercury or a mercury compound such as mercuricoxide is preferred. As examples of other catalysts may be mentioned copper compounds, selenium compounds and various other metallic compounds, which, however, do not give the same good results as mercury compounds.

The reaction may be accelerated by adding oxidating agents, but many oxidating agents will cause partial oxidation of ammonia to elementary nitrogen and result in analytical errors. It is an advantage to use hydrogen peroxide, which in connection with mercury as catalyst may be used essentially without risk of forming free nitrogen. The reason probably is that hydrogen peroxide exerts its oxidating effect during the first step of the heating and is cleaved or removed by distillation before the temperature has reached the actual decomposition temperature.

The use of hydrogen peroxide in combination with a mixture of phosphoric acid and sulphuric acid has already been suggested. The presence of phosphoric acid, however, involves the disadvantage that it produces a certain amount of metaphosphoric acid resulting in the formation of a solid decomposition product with a consequent loss of ammonia.

In the conventional Kjeldahl determination, in the form of macro-analysis, the decomposition usually takes from 30 minutes to 3 hours, for instance 2 hours, even where the decomposition mixture contains potassium sulphate for raising the boiling point and catalyst for accelerating the decomposition. In the procedures described above it will be possible to considerably reduce the decomposition time, and by using micro-methods decomposition times right down to 2–6 minutes have been recorded. The addition of potassium sulphate to the sulphuric acid can only be done up to a certain limit, for normally the boiling point of the mixture should not be allowed to exceed 420°C. At temperatures above this value the ammonia will be cleaved and the analysis will be inaccurate.

After decomposition and cooling of the flask water is added and the mixture is neutralised by adding an excess of sodium hydroxide. The ammonia can then be stripped, preferably by steam distillation.

It is normal practice to collect the ammonia-containing distillate in excess of an accurately measured amount of acid, which is then titrated back with a standardised basic solution. On account of the instability of the basic solutions in the presence of carbon dioxide-containing atmospheric air it would be desirable to perform the titration directly on the distillate with a standardised acid solution. Previous tests in this respect, however, have shown loss of ammonia with resultant considerable analytical errors. But it has been found to be possible to take up the distillate in a boric acid solution which can be titrated directly with standardised acid. This end point appears at a pH of about 4.7, which is favourable because at this pH no errors will be caused by atmospheric carbon dioxide. On account of the buffer effect of the boric acid, however, this method will not produce a very sharp end point and a quite accurate analysis will be difficult to obtain.

In the known procedures it is very difficult to carry out the nitrogen determinations as rapid serial analyses or by automatic methods, particularly as far as macro-analyses are concerned. A condition for doing so would be that the decomposition rate could be considerably increased and that the other process steps could be adjusted to each other and to the decompositon.

The prior art comprises partly automatic analytical apparatus, but they have not been widely applied because they have either been inconvenient in use or produced inaccurate analytical results. One of the known apparatus, for instance, comprises a tube formed as a horizontal spiral which is electrically heated. The samples are introduced successively together with the decomposition mixture. On being passed through the tube the sample is decomposed, and the formed ammonia is analysed, for instance by colorimetry. Such an apparatus, however, can be used only for micro-analysis and is not usually applicable for analysis of complex feedingstuffs and food from which it is difficult to extract uniform characteristic samples of small volume. Moreover, it will only be possible to obtain relatively reliable results if the successive samples are of the same type, because the decomposition conditions have to be adjusted to the type and composition of the samples, and compounds which are decomposable only with difficulty cannot usually be analysed with the required accuracy by this method.

It is the aim of the instant invention to provide an analytical apparatus which is highly automatic and which can be used for carrying out a large number of nitrogen analyses per hour with great accuracy and without requiring a specifically trained staff.

It is a further aim of the invention to provide an apparatus for continuous and automatic nitrogen determinations in which the period of time from the starting of the analysis till the result is obtained has been substantially reduced.

This aim has been accomplished by an apparatus comprising from 4 to 7 flasks suspended vertically in a rotatable roundabout, each provided with a cover and a side tube extending into a common central container for collecting decomposition products, the roundabout being connected to a device which at regular intervals turns the roundabout one step forward into the next position, means for heating the flasks in one or two of the said positions, means for blowing cooling air against the flasks, means for feeding diluent water to the flasks in a subsequent position, means for introducing neutralising chemicals, means for generating and feeding steam to the flasks in the next following position, means for collecting and titrating the distillate, blowing means for emptying the flasks in the last position, and means for opening the covers on completion of the decomposition and introducing diluent water into the flasks.

In this apparatus it is possible to use a decomposition mixture of optimal composition, in that the content of sulphuric acid is adjusted to the fat content of the sample so as to obtain, after decomposition of the organic components of the sample a mixture which has a boiling point between 390° and 420°C, preferably about 410°C. By using such a mixture it will be possible in the said apparatus, even by macro-analysis of a sample of for instance 1 gram, to reduce the decomposition time substantially, for instance to 6 minutes or below. The use of vertical flasks involves the advantage that the dilution of the decomposition product can be made in a partly cooled flask by sprinkling in water so that the sulphur dioxide developed during the dilution of the hot decomposition product is either stripped entirely from the flask or taken up in the water and refluxed to the flask, where it may be neutralised. Otherwise the sulphur dioxide vapours, if carried into the distillate, might result in analytical errors. The vertical suspension of the flasks, moreover, facilitates the automation of all steps of the process, particularly the introduction of the dosaged quantities of chemicals and the means for steam distillation and blowing out of the contents of the flasks on completion of the analysis.

To obtain a short analytical cycle the ammonia is titrated in the distillate immediately after or simultaneously with the stripping, it being possible to collect the distillate in a neutral medium without risking loss of ammonia. This, as pointed out above, cannot be done in a standard analysis, where the distillate is collected in a measured acid solution or in boric acid. When the titration is carried out with an adjusted acid simultaneously with the stripping of the ammonia the titration liquid will constantly be approximately neutral, and it has been found that no loss of ammonia will result. Moreover, the end point is extremely sharp because the titration liquid contains no buffers and the analysis will therefore be very accurate. The procedure has the further advantage that the titration will be completed as soon as the steam distillation is finished. The steam distillation and the titration are therefore conveniently carried out in the same step, which also facilitates automation of the process.

The decomposition may preferably be carried out in two consecutive steps, the first comprising mainly an oxidation with hydrogen peroxide in sulphuric acid while supplying a maximum of heat, the second step including pyrolysis at the boiling point of the potassium sulphate - sulphuric acid mixture while supplying the heat required for boiling. In the first step the heat supply is particularly high because the decomposition product is to be heated rapidly and the oxygen stripped, the major part of the decomposition taking place here.

In the manner described the decomposition will be particularly rapid. Optimal conditions are obtained if the decomposition mixture, in case of macro-analyses, consists of from 8 to 10 ml of hydrogen peroxide of a concentration of from 30 to 35% by weight, from 0.5 to 1 gram of mercury or mercuric compound calculated as mercuricoxide, about 15 grams of potassium sulphate and from 10 to 15 ml of concentrated sulphuric acid dependent on the content of fat in the sample. A smaller amount of hydrogen peroxide than the said 8–10 ml calculated on a concentration of 35% will slow down the decomposition. A larger amount will produce undesirable frothing and involves the risk of partial oxidation of ammonia to free nitrogen. Also the content of water is of significance. A higher content of water, that is a more diluted hydrogen peroxide solution, will delay the decomposition because the water will have to evaporate first. A certain content of water is beneficial, though, because the steam during the initiation of the decomposition will condense in the flask neck and return solid particles which may have been carried upwards to the flask.

To obtain rapid decomposition of substances which are decomposable only with difficulty the boiling point of the mixture must be raised during the last step of the decomposition to a predetermined maximum temperature, preferably about 410°C, irrespective of the composition of the sample, and this presupposes the same final concentration of potassium sulphate and sulphuric acid. In the decomposition 1 gram of carbohydrates consumes 7.3 grams of sulphuric acid for the combustion, while 1 gram of fat consumes 17.8 grams of sulphuric acid and 1 gram of protein about 8.1 grams of sulphuric acid. To obtain a constant composition of the potassium sulphate-acid mixture after the decomposition the added quantity of sulphuric acid has to be adjusted to the fat content of the sample, which is mainly responsible for the consumption of sulphuric acid. An amount of sulphuric acid of from 10 to 15 ml is preferred, as mentioned above, the smaller quantity being used for samples with a low content of fat and the larger quantity for samples with a high content of fat.

Moreover, it will be expedient to add the potassium sulphate in the form of tablets which are compressed so that the potassium sulphate will only dissolve completely in the second step of the decomposition. This obviates inconvenient frothing in the first step of the decomposition with the risk of analytical losses and reduced rate of decomposition. The catalyst may conveniently be admixed in the potassium sulphate of these tablets so as to facilitate dosage.

Dilution of the decomposition product may be effected after cooling down the decomposition flask to 120°–160°C, and in case of macro-analysis 120–150 ml of water is then sprinkled in. This cooling and dilution can easily be adjusted to the other steps to obtain an automatic procedure. Possible drops of splashed up decomposition product on the inner surface of the flask neck will be flushed back with the sprinkled water, and free $SO_2$ will be taken up in the diluent water.

The said apparatus is particularly suitable for nitrogen determination of a large number of samples which are passed successively through a plurality of steps, preferably six.

In an expedient embodiment of the apparatus the means for collecting and titrating the distillate consist in a cylindrical glass vessel within a photocell arrangement projecting a vertical light beam through the cylindrical glass vessel and a feeding device for titration liquid controlled by the photocell arrangement.

A preferred embodiment of the apparatus is arranged so that in each position the roundabout is provided with a magnetic indicator which is activated on the feeding of the dosage quantities into the corresponding flask but will remain inactivated if the flask is not provided with a sample and decomposition chemicals. In the activated state the magnetic indicator connects the heat supply to the decomposition flask and the means for introducing the neutralisation chemicals, the means for feeding steam and the means for collecting and titrating the distillate. This construction of the apparatus ensures a reliable operation even if one or more of the flasks are not used in the analysis.

It will also be expedient to provide the apparatus with a drop catcher consisting of two flasks communicating through a tube, the steam feeding pipe being carried through the first flask into the analytical flask, and the said tube thus extends from the first flask and tangentially into the second, which is provided with a discharge pipe issuing from a point at or adjacent to the centre of said second flask and connected to a strong condenser.

The said drop catcher is of extremely high capacity and permits rapid passage of vapour without risk of carrying drops of liquid along.

Figure 2:
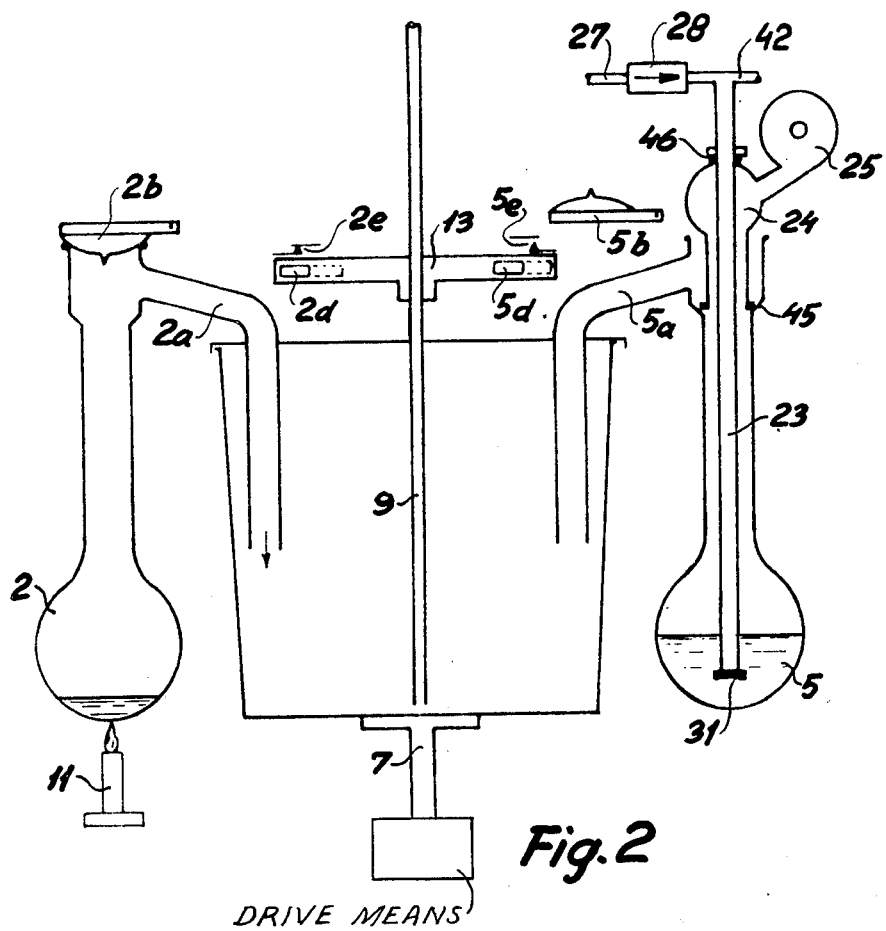

The apparatus according to the invention will be explained in greater detail below with reference to the drawing, in which FIG. 1 is a schematic illustration of an apparatus according to the invention viewed from above and FIG. 2 shows a transverse section of the same apparatus.

FIGS. 1 and 2 show an apparatus comprising six flasks 1, 2, 3, 4, 5, 6 vertically suspended in a roundabout revolving about a vertical central axis (7), so that the flasks by revolving stepwise, 60° in each step, may hold six different positions.

The flasks 1–6, which are of a heat resistant glass, have openings 1c–6c at the top which are sealable by covers 1b–6b. They are shown in the sealed state in positions 2, 3 and 4 and with the covers removed, that is open, in positions 5, 6 and 1. The covers are provided with ground joints for sealing the openings of the flasks airtight. The flasks 1–6 have side tubes 1a–6a at the top, all extending downwards into the central container 8 of acid resistant material, such as polyethylene. A suction pipe 9 is introduced into the container 8 and connected to a water jet air pump (not shown) for removing decomposition products and other waste from the container 8. The roundabout is connected to a means (not shown), for instance a time-controlled motor, which at certain intervals of for instance 3 minutes turns the roundabout with the flasks 1–6 60° in the direction indicated by the arrow 10. Under the flask 2 in the second position is a gas burner 11 for heating the flask 2 and under the flask 3 in the 3rd position is also a gas burner 12 for heating the flask 3. Over the container 8 is a rotating disc 13 that follows in the movement of the roundabout. Opposite each position the rotating disc 13 is provided with a magnet 1d–6d which by the action of an electromagnet 14 can be adjusted between two positions, remote from and nearer to the centre. The positions of the magnets 1d–6d can be read by means of reed contacts 2e–5e, and the magnets can be reset by means of a permanent magnet 16.

The flask 4 in the 4th position is connected to a cooling means 17 in the form of a fan for the blowing of cold air and a sprinkler 18 for the sprinkling of water. The cover 4b is opened by means of a device which may comprise an arm 20 actuated by a gear motor 21. The opening of the cover 4b and the sprinkling of water through the opening are controlled by a clock switch 22.

In the 5th position steam is supplied through an inlet pipe 23 terminating in a porous distributor plate 31. The pipe 23 is connected to and passes through a drop catcher 24, 25. The steam is generated by heating a flask 26 filled with water and is conducted through a pipe 27 and a valve 28 to the pipe 23.

The ammoniacal steam passes through the drop catcher 24, 25 and a pipe 30 to a condenser 32 which is connected to cooling water that enters the jacket at 33 and leaves through an outlet tube 34. The condensate from the condenser 32 is led into a titration vessel 35 which is maintained in agitation by means of an impeller 36. The titration liquid (for instance an adjusted sulphuric acid solution) is introduced at 37 and the indicator solution at 38. The drawing further shows a photocell 39 which is exposed to light from a lamp 40 with a lens 41.

The described apparatus may be operated continuously and automatically so that the sample under examination and decomposition chemicals may be fed for instance every 3 minutes through the opening 1c of the flask 1 in the first position.

With a sample of for instance 1 gram is used from 8 to 10 ml of hydrogen peroxide of a concentration of 30–35 percent by weight and from 10 to 15 ml of concentrated sulphuric acid dependent on the fat content of the sample. The addition may be carried out manually but it will be expedient to dose the liquids automatically by dosing means (not shown) of known description, for instance a pump or syringe.

Moreover 15 grams of potassium sulphate is added and from 0.7 to 0.8 gram of mercuric oxide as catalyst. To obtain an easy and accurate dosage and avoid damage to the flasks it will be advisable to feed the two chemicals manually in the form of a homogeneous mixture distributed in compressed tablets, for instance 3 of 5 grams each. After addition of the chemicals the cover 1b is fitted. At the stipulated time the roundabout rotates all the flasks 60° so as to bring the flask forward to the 2nd position, indicated at the flask 2. The flask 2 is heated by the gas burner 11, whereby the decomposition is initiated. The vapours generated during decomposition pass through the side tube 2a and accumulate in the central container 8, from which they are removed through the suction pipe 9, for instance by means of a water-jet air pump (not shown).

On the next turning of the roundabout the sample reaches the third step indicated by the flask 3. This flask is heated by means of the gas burner 12 to complete the decomposition at about 410°C. The decomposition period is thus two intervals each of 3 minutes. In the fourth step the flask 4 is cooled by cooling air from the fan 17. In the example it was found that the contents of the flask were cooled to about 130°C in slightly less than 3 minutes, and at this temperature diluent water is added through the sprinkler 18 after the cover 4b has been opened automatically by means of an automatically controlled lifting arm 20.

It has been found to be expedient to add the diluent water by sprinking since thereby it will be possible to prevent the sulphur dioxide developed by the dilution of the hot sulphuric acid from rising as vapour and being carried in the titration liquid in the following steam distillation. Sulphur dioxide vapours are taken up in the sprinkled water and carried into the flask.

In the fifth position the steam feeding pipe 23 is lowered into the flask, the neck opening of which is sealed with a gasket 45. Directly thereafter sodium hydroxide solution is fed to the flask 5 through the tubes 42 and 29 from a container 43 by means of a dosage arrangement 44, for instance an automatically controlled magnet valve. The sodium hydroxide solution is distributed in the contents of the flask by being passed through a strainer 31 so as to avoid squirting that might be caused by the vigorous development of heat during neutralisation. The tube 23 is carried through the drop catcher 24, 25 where the lead-in is sealed with a gasket 46. The steam is generated in the flask 26 and carried through the tubes 27 and 23 and through the strainer or disributing disc 31. The ammonia-containing vapours pass the drop catcher 24, 25 and are condensed in the condenser 32, from which the condensate drips into the titration vessel 35. In the vessel there has previously been introduced a measured amount of indicator dissolved in distilled water. The titration is effected by the addition of a standardised acid solution through the tube 37 simultaneously with the dripping of the ammonia-containing condensate into the titration liquid. The addition of the acid solution is controlled automatically by colorimetric measurement of the indicator end point by means of a photocell 39 which is exposed to light from a lamp 40 through the lens 41. By carrying out the titration in this way, where the solution is constantly approximately neutral, it will be possible to titrate with acid instead of accumulating the distillate in an acid and titrating back with a base. This constitutes a substantial simplification of the process and enables automatic operation of the apparatus. Besides it produces a very sharp end point.

The volume of acid to be used in the titration is measured automatically, for instance by recording the position of a piston in a dosage device (not shown). In the colorimetric titration is used a vertical light beam, whereby the light absorption is maintained constant even if the liquid volume is increased by the addition of distillate and titration liquid, because the level of the liquid is raised correspondingly.

When the titration is finished the flask is turned into the 6th position, where the contents are blown out by means of compressed air into the central discharge container 8. The contents of the discharge container is maintained at a constant value by automatic suction of excess liquid.

The system described here may be provided with conventional control and register arrangements so that the analyses can be performed virtually fully automatically. The concentrated sulphuric acid, for instance, may be dosaged by the operation of a starting lever which is operated on the introduction of a sample to be analysed and which at the same time actuates the electromagnet 14 to attract the permanent magnet 1d. By means of reed contacts 2e–5e the position of the magnets in the various steps may be read and the operations controlled. If, for instance, no sample or decomposition chemicals are fed to a flask the magnet 1d will not be attracted to the extreme position and the supply of gas, the supply of steam, and the titration will not be activated. The result of the analysis may be read on an instrument or written automatically by a printer. The water level in the flask 26 can be kept constant by suspending the flask in a lever 46 connected to a contact 47 which controls a magnet valve 48 connected to the supply of water.

The system may likewise be provided in known manner with safety means for arresting the operation of the apparatus if the gas or water supply fails or if a cover sticks. The apparatus is also provided with safety means for arresting the operation if the sprinkling of diluent water fails so as to obviate the risk of introducing neutralizing chemicals into the decomposition product containing concentrated sulphuric acid.

What I claim is:

1. An analytical apparatus for serial determination of nitrogen in samples by the Kjeldahl method, comprising:
   a. a roundabout;
   b. a plurality of flasks suspended vertically by the roundabout, each flask being provided with a cover and a side tube;
   c. means for removing decomposition products;
   d. drive means connected to rotate the roundabout stepwise to bring each flask in succession to a first position and advance each flask from the first position into several intermediate positions in succession and bring it back to the first position;
   e. means for introducing sample material and decomposition material into the flask in the first position;
   f. means for heating the flask in at least one subsequent intermediate position;
   g. means for cooling the flask in a following position;
   h. means for feeding diluent water into the flask in said following position;
   i. means for introducing neutralizing material and steam into the flask in a further following position;
   j. means for titrating the distillate from the flask in the said further following position;
   k. means for emptying the flasks in the last said intermediate positions;
   l. means for removing the covers on the completion of decomposition.

2. An apparatus according to claim 1, wherein the number of flasks is six and the drive means are arranged to rotate the roundabout in steps of 60°.

3. An apparatus according to claim 1, comprising a cylindrical glass vessel for collecting said distillate, a photocell arrangement projecting a vertical light beam through the cylindrical glass vessel, and a feeding device for titration liquid coupled to and controlled by said photocell arrangement.

4. An apparatus according to claim 1, wherein the roundabout is provided with a plurality of magnets respectively associated with said flasks, and that magnet which is associated with that flask which is in said first position is activated on the feeding of a sample into a flask but remains inactivated if the flask is not supplied with sample material and decomposition material, and wherein when that magnet which is associated with the flask in said subsequent position is in the activated state it initiates supply of heat to said flask, and when that magnet which is associated with the flask in said further following position is in the activated state it initiates introduction of neutralizing material and steam into said flask and collection and titration of distillate from said flask.

5. An apparatus according to claim 1, wherein the means for introducing steam into the flask in said further following position includes a steam feeding pipe, and a drop catcher comprising first and second bulbs interconnected by a tube which opens tangentially into the second bulb, the steam feeding pipe extending through the first bulb, and the second bulb being provided with a discharge tube issuing from a point at or adjacent to the centre of the second bulb and communicating with a condenser.

6. An apparatus according to claim 1, wherein the means for removing decomposition products comprise a container for collection of decomposition products, said container being disposed centrally of the flasks and having the side tubes extending thereinto.

7. An apparatus according to claim 1, wherein the means for emptying the flasks comprise blowing means.

* * * * *